(12) United States Patent
Hakkala et al.

(10) Patent No.: US 9,615,628 B2
(45) Date of Patent: Apr. 11, 2017

(54) INSOLE AND A METHOD AND A SYSTEM FOR INSOLE MANUFACTURE

(75) Inventors: Erkki Hakkala, Helsinki (FI); Patrik Louko, Helsinki (FI)

(73) Assignee: FOOTBALANCE SYSTEM OY, Helsinki (FI)

( * ) Notice: Subject to any disclaimer, the term of this patent is extended or adjusted under 35 U.S.C. 154(b) by 1031 days.

(21) Appl. No.: 13/508,160

(22) PCT Filed: Nov. 4, 2009
(Under 37 CFR 1.47)

(86) PCT No.: PCT/FI2009/050890
§ 371 (c)(1),
(2), (4) Date: Nov. 23, 2012

(87) PCT Pub. No.: WO2011/054999
PCT Pub. Date: May 12, 2011

(65) Prior Publication Data
US 2013/0174445 A1    Jul. 11, 2013

(51) Int. Cl.
*A43D 35/00*    (2006.01)
*A43B 13/38*    (2006.01)
(Continued)

(52) U.S. Cl.
CPC .............. *A43B 13/386* (2013.01); *A43B 7/28* (2013.01); *A43D 1/02* (2013.01); *A43D 1/022* (2013.01);
(Continued)

(58) Field of Classification Search
CPC . A43D 35/00; A43D 1/00; A43D 1/02; A43D 1/025; A43D 39/00; A43B 7/141
(Continued)

(56) References Cited

U.S. PATENT DOCUMENTS 1,826,783 A * 10/1931 Fritz ...................... B21D 37/02
33/514.2
4,212,188 A    7/1980 Pinson
(Continued)

FOREIGN PATENT DOCUMENTS

CN    1627038 A    6/2005
CN    1809724 A    7/2006
(Continued)

OTHER PUBLICATIONS

JP Office Action dated Oct. 29, 2013 from corresp JP 2012-537427—English translation.
(Continued)

*Primary Examiner* — Ted Kavanaugh
(74) *Attorney, Agent, or Firm* — Young & Thompson

(57) ABSTRACT

A method, apparatuses and a system for manufacturing an insole, a shoe or a sole for a shoe. Foot information is determined on the shape and dimensions of a foot, and a pin matrix is formed at least partially based on the foot information. An insole or sole preform is placed on the pin matrix for shaping the insole preform, and an insole or sole is formed from the preform based on the foot information using the pin matrix. A positive and a negative pin matrix at least partially based on the foot information can be formed wherein the negative pin matrix essentially corresponds to the positive pin matrix.

7 Claims, 9 Drawing Sheets

(51) Int. Cl.
  *A43D 1/02* (2006.01)
  *A43B 7/28* (2006.01)
  *A61B 5/107* (2006.01)
  *G01B 11/25* (2006.01)
  *G05B 15/02* (2006.01)

(52) U.S. Cl.
  CPC ............ *A43D 1/025* (2013.01); *A61B 5/1074* (2013.01); *G01B 11/25* (2013.01); *G05B 15/02* (2013.01)

(58) Field of Classification Search
  USPC ........................ 12/21, 146 B, 146 BP, 146 M
  See application file for complete search history.

(56) References Cited

U.S. PATENT DOCUMENTS

| | | | |
|---|---|---|---|
| 4,449,264 A | 5/1984 | Schwartz | |
| 4,517,696 A * | 5/1985 | Schartz | A43D 1/00 12/1 R |
| 4,876,758 A | 10/1989 | Rolloff et al. | |
| 5,640,779 A | 6/1997 | Rolloff et al. | |
| 6,160,264 A | 12/2000 | Rebiere | |
| 6,168,741 B1 * | 1/2001 | Foldes | A43B 1/0027 264/244 |
| 6,904,692 B2 | 6/2005 | Tadin | |
| 2004/0245428 A1 | 12/2004 | Moshe et al. | |
| 2008/0097720 A1 | 4/2008 | Tadin et al. | |
| 2009/0183389 A1 * | 7/2009 | Miller | A43B 7/141 36/43 |

FOREIGN PATENT DOCUMENTS

| | | |
|---|---|---|
| JP | 63-257506 | 10/1988 |
| JP | 3152863 | 7/2009 |
| WO | 2008006937 A1 | 1/2008 |

OTHER PUBLICATIONS

International Search Report, dated Jun. 15, 2010, from corresponding PCT application.
Chinese Office Action, dated Sep. 2, 2014, from corresponding CN application.

* cited by examiner

INSOLE AND A METHOD AND A SYSTEM FOR INSOLE MANUFACTURE

FIELD OF THE INVENTION

The present invention relates to methods for manufacturing insoles, especially heat-formable customized insoles for footwear, and to manufacturing footwear, for example shoes and soles for shoes. The present invention also relates to apparatuses and systems for manufacturing customized insoles and shoes, as well as customized insoles, soles for shoes and shoes manufactured according to the invention. The invention also relates to corresponding footwear, and method for manufacturing such footwear like shoes.

BACKGROUND

Most of the people in the world population suffer from some sort of foot problems. Foot motion/gait problems reflect to soles, ankles, knees, hips, back, etc; that is why their treatment and prevention is particularly beneficial to the whole human well-being. An individual takes around 15 000-16 000 steps every day. The load on feet in sports is many times the weight of the body. For example, the ground force is about three times one's body weight while running and 7.5 times while playing basketball due to jumps and other irregular moves. Provided that the foot position is correct, the load divides evenly between the upper joints.

A common condition called pronation refers to inward (i.e. medial) roll of the foot (especially heel and arch), which turns into overpronation when the foot rolls too much. In contrast, oversupination is caused by too small inward roll. Both conditions easily cause pain, wear and even stress injuries in the feet and various body joints.

Different (arch) support insoles are available for correcting the foot position. They have been designed to support longitudinal medial and lateral arch but without separately glued wedges they do not actually correct foot position. Wedging is a time-consuming and expensive process. The obtained result depends on the person doing the task and still tends to be rather inaccurate. As another drawback, after gluing the wedges to the soles one cannot take a new mold without first removing the wedges.

Ready-made supports in the insoles do not generally provide a perfect match to anyone's feet, as people do not generally bear identical feet shape. Accordingly, many support insoles are ultimately deemed inconvenient due to their lousy fit. Only few of the people suffering from foot problems have had a chance to purchase insoles that alleviate at least part of the problems. Traditionally, custom-made shoes and insoles have been manufactured by professional shoe-makers, physio-therapists, or podiatrists.

So far the associated purchase process has been rather time-consuming and costly. Measuring the feet and manufacturing the insoles requires expensive and specialized apparatuses, and yet the speed at which the manufacturing can take place is limited. Naturally, these circumstances increase the cost of custom-made insoles, as well, which makes them less affordable to people suffering from foot problems.

There is, therefore, a need for a solution that improves the overall process of ordering and manufacturing insoles, as well as for improvements in the manufacturing technology of insoles.

SUMMARY

Now there has been invented an improved method and technical equipment implementing the method, by which the above problems are alleviated. Various aspects of the invention include a method, an apparatus, a system and an insole, which are characterized by what is stated in the independent claims. Various embodiments of the invention are disclosed in the dependent claims.

According to a first aspect, there is provided a method for manufacturing an insole or a sole of a shoe, or a shoe at an apparatus, comprising determining foot information on the shape and dimensions of a foot, forming at least one at least partial pin matrix at least partially based on the foot information, positioning an insole or a sole preform on said at least one at least partial pin matrix for shaping said insole or sole preform, and forming an insole or sole from an insole or sole preform based on said foot information. According to an example embodiment, the method comprises forming at least one at least partial positive pin matrix at least partially based on the foot information. According to an example embodiment, the method comprises forming at least one at least partial negative pin matrix at least partially based on the foot information wherein said at least one at least partial negative pin matrix essentially corresponds to the at least one at least partial positive pin matrix. According to an example embodiment, the method comprises positioning an insole preform between said at least one at least partial positive pin matrix said and at least one at least partial negative pin matrix for shaping said insole or sole preform. According to an example embodiment, the method comprises electronically storing said foot information at a computer in a database of foot information, and electronically retrieving said information on the shape and dimensions of a foot at a computer from a database of foot information for shaping said insole or sole. According to an example embodiment, the method comprises determining said foot information using a scanning system. According to an example embodiment, the method comprises forming said at least one at least partial pin matrix using a robot for example such that said robot has a roller head for rolling over the pins of the said at least one at least partial pin matrix.

According to a second aspect, there is provided an apparatus for manufacturing an insole or a sole of a shoe comprising a first pin matrix adapted for giving shape to an insole or sole preform. According to an example embodiment, the apparatus comprises a second pin matrix essentially corresponding to the first pin matrix, the second pin matrix being adapted for giving shape to the insole or sole preform, and the apparatus being adapted to give shape to the insole or sole preform by pressing the insole or sole between the first pin matrix and the second pin matrix. According to an example embodiment, the apparatus comprises a module for forming or receiving information on a shape of a foot, and a module for adapting at least one of the first pin matrix and the second pin matrix to give shape to the insole preform by moving pins of at least one of the first pin matrix and the second pin matrix according to the information on the shape of the foot. According to an example embodiment, at least the first pin matrix is adapted to form a shape according to the information on the shape of the foot by moving pins of the pin matrix and locking them in position. According to an example embodiment, the second pin matrix is adapted to adjust to the shape of the first pin matrix when the second pin matrix is being pressed against the first pin matrix. According to an example embodiment, one of the first pin matrix and the second pin matrix is a positive pin matrix and the other one of the first pin matrix and the second pin matrix is a negative pin matrix. According to an example embodiment, the apparatus comprises memory for storing information on a shape of the a foot and a processor for adapting the first pin matrix according to said information on the shape of the foot in said memory. According to an example embodiment, the apparatus comprises computer program code for causing the apparatus to store the information on the shape of the foot in a database where the information on the shape of the foot is retrievable for giving shape to an insole or sole preform. According to an example embodiment, the apparatus comprises a scanner for determining information on a shape of a foot.

According to a third aspect, there is provided a system comprising a processor, memory including computer program code, the memory and the computer program code configured to, with the processor, cause the system to at least determine foot information on the shape and dimensions of a foot, form an insole or sole of a shoe from an insole or sole preform based on said foot information, form at least one at least partial pin matrix at least partially based on the foot information, and position an insole or sole preform on said at least one at least partial pin matrix for shaping said insole or sole preform. According to an example embodiment, the system comprises computer program code to, with the processor, cause the system to at least form at least one at least partial positive pin matrix at least partially based on the foot information. According to an example embodiment, the system comprises computer program code to, with the processor, cause the system to at least form at least one at least partial negative pin matrix at least partially based on the foot information wherein said at least one at least partial negative pin matrix essentially corresponds to the at least one at least partial positive pin matrix. According to an example embodiment, the system comprises computer program code to, with the processor, cause the system to at least position an insole or sole preform between said at least one at least partial positive pin matrix said and at least one at least partial negative pin matrix for shaping said insole or sole preform. According to an example embodiment, the system comprises computer program code to, with the processor, cause the system to at least electronically store said foot information at a computer in a database of foot information, and electronically retrieve said information on the shape and dimensions of a foot at a computer from a database of foot information for shaping said insole or sole. According to an example embodiment, the system comprises computer program code to, with the processor, cause the system to at least determine said foot information using a scanning system. According to an example embodiment, the system comprises computer program code to, with the processor, cause the system to at least form said at least one at least partial pin matrix using a robot for example such that said robot has a roller head for rolling over the pins of the said at least one at least partial pin matrix.

According to a fourth aspect, there is provided an insole and a shoe having been produced using a method according to the first aspect of the invention. According to a fifth aspect, there is provided shoe comprising an insole having been produced by a method according to the first aspect of the invention. An insole, a sole or a shoe having been produced according to the invention may display signs of manufacture by a method according to the invention, for example it may show pressure marks of pins from pin matrices on one side, on both sides or in the inner layers of the insole or sole. The insole or sole may also be specially formed due to the heating or cooling properties of a method according to the invention. Such signs of manufacture may be intentionally created or they may be formed in the manufacturing process naturally without intention.

DESCRIPTION OF THE DRAWINGS

In the following, various embodiments of the invention will be described in more detail with reference to the appended drawings, in which.

DETAILED DESCRIPTION OF THE EXAMPLE EMBODIMENTS

In the following, several embodiments of the invention will be described in the context of a system for manufacturing insoles. It is to be noted, however, that the invention is not merely limited to such a system. In fact, the different embodiments have applications in any environment where customized manufacturing from preforms is used. Especially the manufacturing of shoes may take place in a similar manner as manufacturing insoles. Also, different kinds of foot support footwear may be manufactured according to the embodiments of the invention and may have characteristics similar to insoles created according to the invention. In this line of thought, a shoe may be understood to be any kind of footwear or device intended to be worn on foot.

Figure 1A:
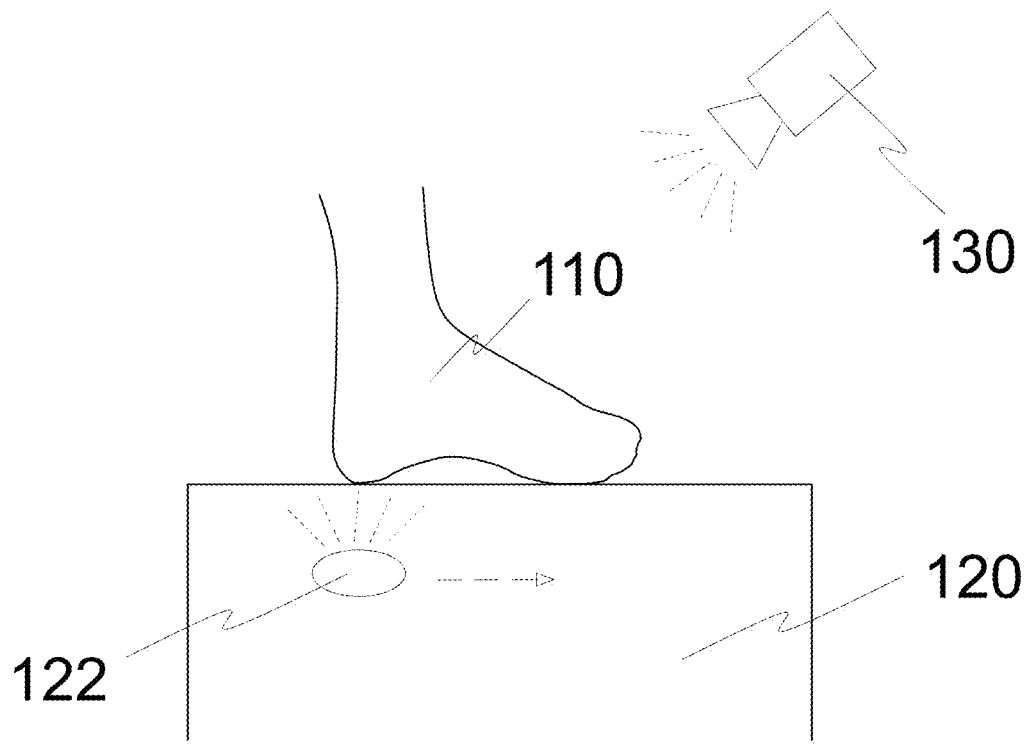
FIG. 1a shows a foot scanning device with optical means for reading the shape of the foot according to an embodiment of the invention.

FIG. 1a shows a foot scanning device with optical means for reading the shape of the foot according to an embodiment of the invention. The foot scanning arrangement may include, for example, a podoscope 120, a camera system 130, and a computer (not shown). The podoscope is, by definition, a device for analysing the interaction of the foot and a supporting surface. A person stands on a transparent glass plate of the podoscope, whereupon an image of his feet may be shown through a mirror to the person doing the measurements for manual operation. The foot scanning arrangement, e.g. aforesaid podoscope, may also include data acquisition means such as an optical scanner 122, a camera 130, or some other suitable apparatus for optically and/or electrically imaging the person's feet and their position (and position errors). The imaging of the person's feet may happen from the bottom using a scanner 122 or a camera underneath the glass plate. The imaging may also be done with the help of a camera 130 from the top, and the bottom of the foot may be imaged using a mirror. From the imaging, measurements of the dimensions and shape of the foot may be determined. If necessary, the device may be calibrated to ensure accurate measurements. Such an arrangement enables storing person-dependent data for future use and archiving purposes. It is possible to store information related to the whole foot or only part of the foot, depending on needs.

Laser scanning is an alternative method for foot scanning. In laser scanning, the determination of the distance to the target, i.e. scanning, may happen using a time-of-flight technology, where the distance is measured by measuring the time of flight of the laser beam to the target and back. For small objects such as the foot, other technologies like phase or interference detection, triangulation and multiple-camera appraches may be used. In such technologies, the phase of modulated light may be used to measure the shape of the target, and/or the angle between the laser transmitter and the camera detecting the reflected laser may be used. In laser based foot scanning the imaging resolution is typically on the order of 1 mm. A plantar foot scanner based on a stereo imaging providing a 3D image with 0.5 mm resolution may be used.

Figure 1B:
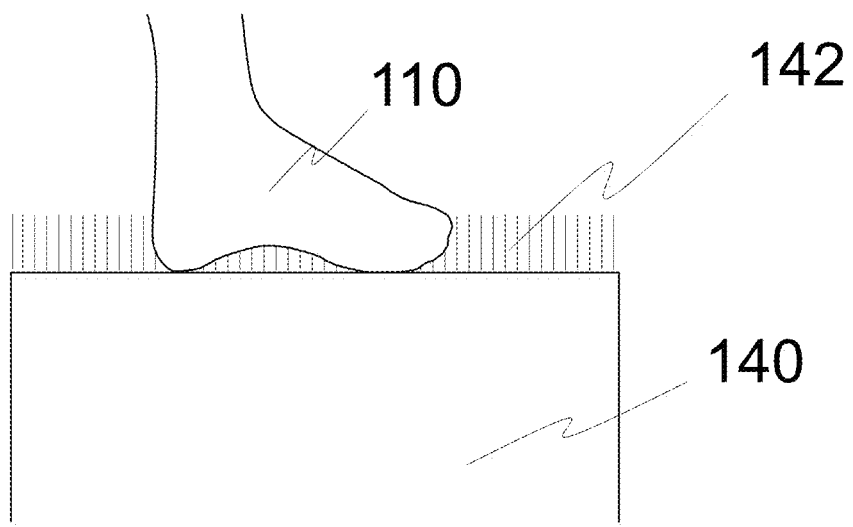
FIG. 1b shows a foot scanning device with mechanical means for reading the shape of the foot according to an embodiment of the invention.

FIG. 1b shows a foot scanning device with mechanical means for reading the shape of the foot according to an embodiment of the invention. In a mechanical foot scanning arrangement, a pin matrix device 140 may be used. In a pin matrix device, a plurality of pins 142, arranged in a regular matrix or irregular setting, are used to measure the distance of the foot 110 from the surface. The pins 142 may be spring-loaded (not shown) so that they yield softly to pressure by the foot, and they may have a locking mechanism (not shown) so that the pin locks into place when needed and the shape of the foot remains in the pin matrix. The pin matrix may also be connected to or contain sensors for reading the individual pin positions, thereby allowing digitization of the foot shape and to form digital information on the shape and dimensions of the foot. The pin matrix may also function so that the foot surface is scanned in a serial manner where each pin can be individually actuated to measure the position of the surface at that location. It is possible to store information related to the whole foot or only part of the foot, depending on needs, and thereby a whole or only a partial pin matrix may be used.

Figure 2A:
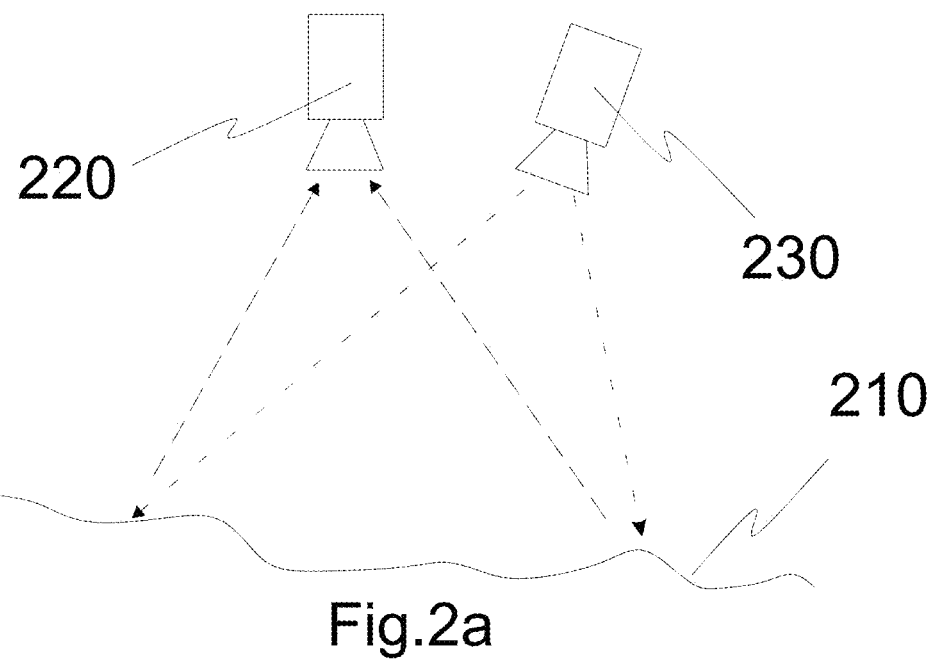
FIGS. 2a and 2b show an operating principle of a foot scanning device with optical means for reading the shape of the foot according to an embodiment of the invention.
Figure 2B:
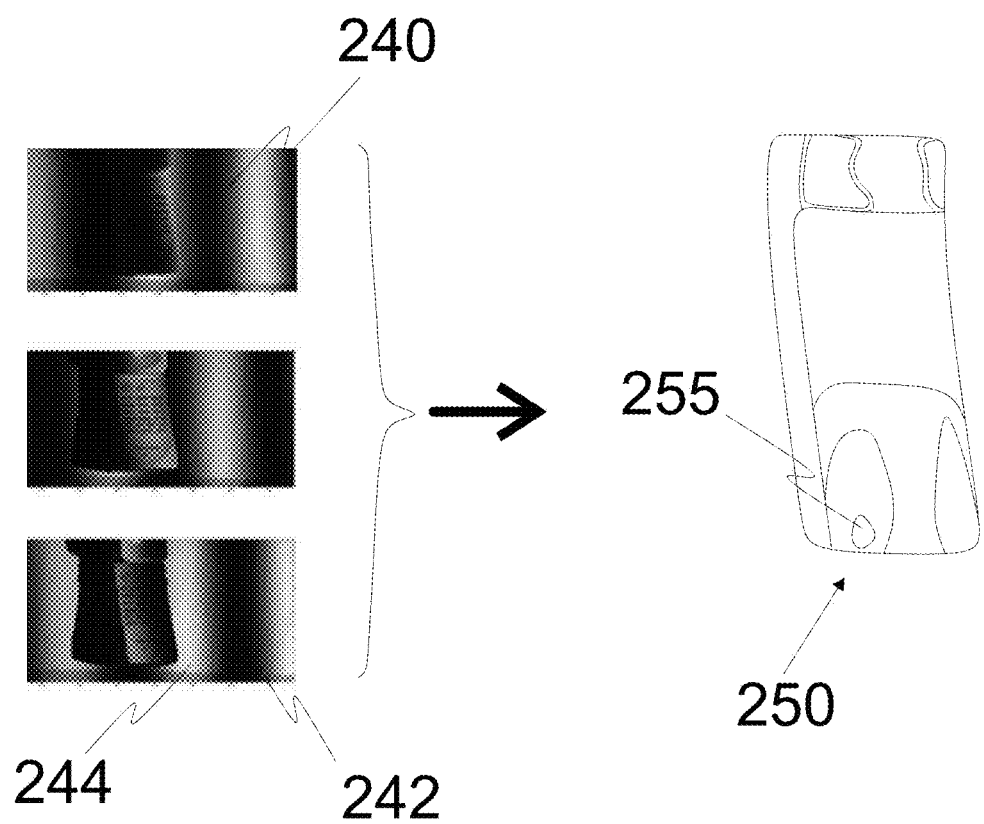

FIGS. 2a and 2b show an operating principle of a foot scanning device with optical means for reading the shape of the foot according to an embodiment of the invention. As shown in connection with FIG. 1, the shape of the plantar foot surface 210 may be scanned with 3D imaging technology suitable for the industrial measurements of dimensions and shape of components and other surfaces. The 3D imaging is based on the target illumination by means of a light source 230 with modulated or structured light and recording the resulting image with a camera 220. In the scanning method, an illumination pattern 240 of sinusoidal fringes that is projected on a surface may be used. The fringe images may be recorded with a digital still camera and/or a video camera. 3D contours of the surface modulate the phase of the fringe pattern seen from the camera's point of view. Thereby, the emitted pattern that changes smoothly from black 242 white 244 receives a more complex structure. This structure can be processed to calculate the phase shift caused by this modulation, and thereby the 3D shape 250 of the surface can be determined. Multiple scans may be performed where the modulation of the light is shifted to illuminate the whole target area. To increase accuracy, different modulation wavelengths may also be used. As a result, information on the height of the object from the base plane may be determined, as shown in FIG. 2b with contours 255. The method may also generate a normal black and white image if needed.

The foot scanning system may have the following specifications. The foot shape may be measured through a glass plate of size 400 mm×400 mm, 0 to 50 mm from the top surface of the glass plate with 0.5 mm, 0.1 mm or 1.0 mm accuracy or any accuracy between 0.01 mm and 1 cm. Both feet may be scanned at the same time, or only one foot at a time, and a scan may take a few seconds, some tens or hundreds of seconds or even a shorter time than a few seconds. The measurement information from the foot scanner is collected to a computer such as a PC, a mobile phone, personal digital assistant (PDA), a laptop computer, a computer in the network, a mainframe computer or other computer for image processing. The computer may also provide an user interface for the operator, and the user interface may be visual, tactile or audio-based. The scanner system may also take photographs from customer's feet and ankles from front and back that may be required for the foot analysis. In addition to or instead of the foot, an already existing insole, shoe or a mold may be scanned. This may be easier than scanning the foot, and/or the scanned insole, shoe or mold may be used as a reference or control for the foot scanning.

Figure 3:
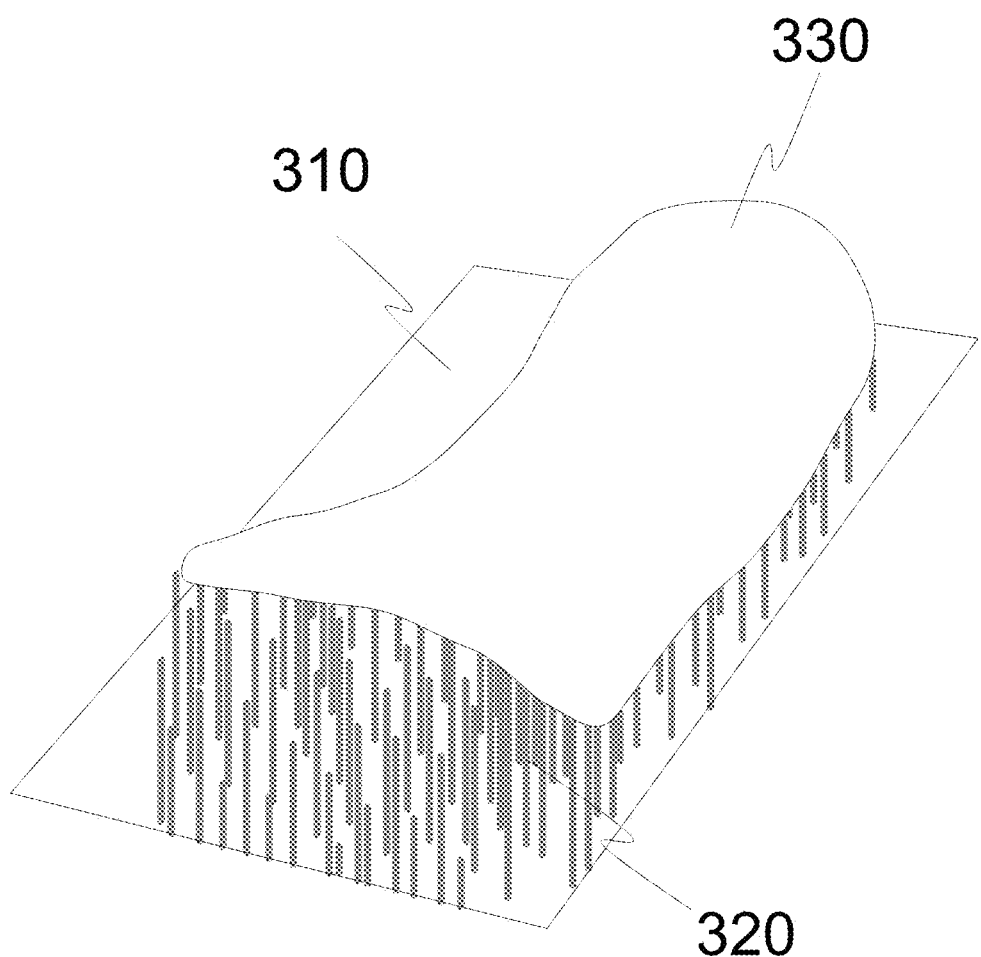
FIG. 3 shows a pin matrix device for forming a heated insole or sole according to an embodiment of the invention.

FIG. 3 shows a pin matrix device for forming a heated insole or a shoe, or a sole for a shoe according to an embodiment of the invention. Traditionally, insoles or soles of shoes have been created by mechanical milling of either the insole or sole or the mold used for fabricating the insole or sole. Such methods may not be suitable for some heat-formable materials. Fabricating a pair of custom insoles by milling may also take about 10-60 minutes, which may also prevent the use of such a system for high-volume production. In an embodiment according to the invention, a pin matrix 310 is formed to have the shape of the foot by using information on the shape and dimensions of the foot to adjust each pin 320 to an appropriate position. After that, a thermo-formable insole preform 330 is placed on the shaped pin matrix in a fabrication unit. Finally, the formed preform may be cooled either passively or actively by blowing air or conducting the heat from the preform through the pins or by other means. The pin spacing in the pin matrix may be a few millimeters, e.g. 1 mm, 3 mm, 6 mm, 8-12 mm or even 10-20 mm or anything of the kind depending on the pins. A smaller pin spacing may improve the accuracy of the fabrication process to achieve a good fit to the foot, while a larger pin spacing may make the process faster and facilitate easier operation during manufacture. A support sheet of some suitable material like silicone may be used between the pin matrix and the insole preform during fabrication. Such a support sheet may spread the pressure on the preform from the pins more evenly. The pins may have different shape such as hexagonal, square, round, ball-pointed or other shapes suitable for the application.

Figure 4A:
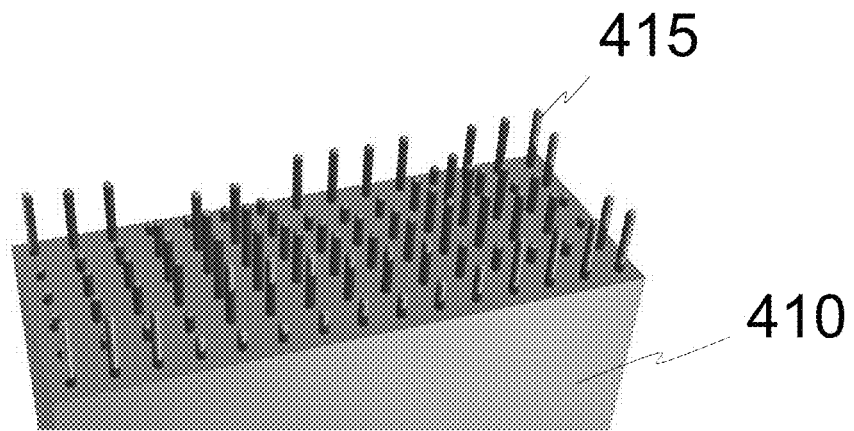
FIGS. 4a, 4b and 4c show a dual pin matrix device for forming a heated insole or sole according to an embodiment of the invention.
Figure 4B:
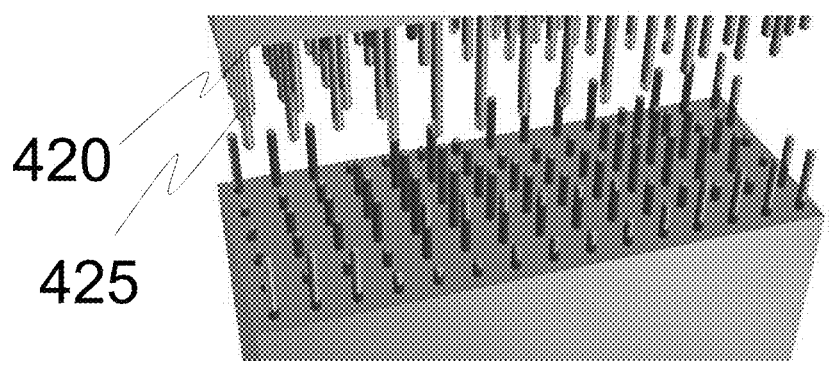
Figure 4C:
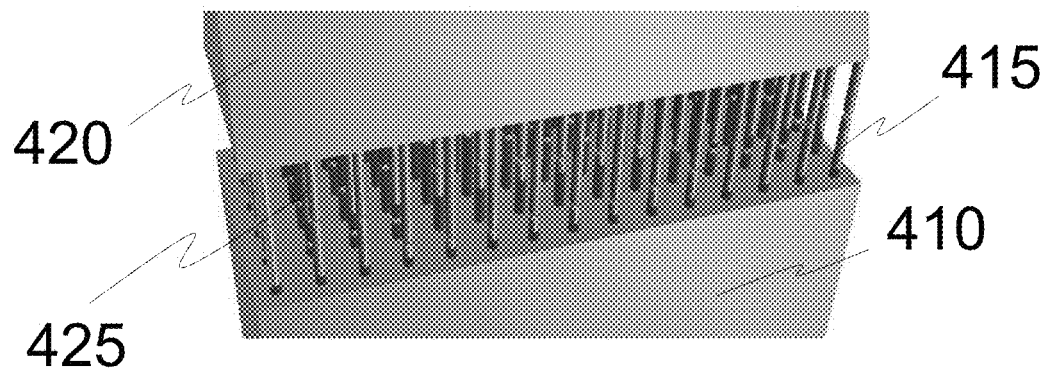

FIGS. 4a, 4b and 4c show a dual pin matrix device for forming a heated insole, a shoe or a sole for a shoe according to an embodiment of the invention. The automated insole or sole fabrication system is based on a pin matrix 410, which will be formed to the shape of the person's foot by loading information on the shape and dimensions of a foot from a database or by otherwise using the information at the apparatus to form the pin matrix. The pin matrix may consist of spring-loaded, self-locking pins 415 that may be simultaneously released or individually released for fast setting and reset.

An arm robot e.g. with six degrees of freedom may be used to shape the matrix to the form of person's foot surface. An appropriate robot and tool selection combined with an optimized control software may allow setting the matrix with few complex tool movements thereby removing the need for manipulating the pins individually. The robot may be equipped with a tool to form the matrix such as a roller head, where the robot may roll over the rows of pins one by one. The robot may have rollers of different sizes to speed up the process, since there may be areas of the pin matrix with the desired pin position around same height. The rolling may be done in phases, where a first rough sweep in multiple rows to get close to required shape is performed first and then another step is carried out row by row to get to the exact pin heights.

In FIG. 4b, a dual pin matrix for fabrication of insoles or soles for shoes is shown, where a lower pin matrix of FIG. 4a is complemented with an upper pin matrix 420 having pins 425 at least partially and essentially corresponding to the pins of the lower pin matrix. The upper pin matrix 420 may be formed in a similar manner as the pin matrix 410. Alternatively, the pin matrix 420 may be formed by forming first the pin matrix 410, locking the pins 415 in position and forming the other pin matrix 420 by pressing it against the formed and locked matrix 410. The order in which the pin matrices are formed may also be reversed so that the pin matrix 420 is formed first. In this process, so-called positive and negative pin matrices are formed so that they correspond to each other and so that the insole preform can be positioned between the pin matrices 410 and 420 for forming, as shown in FIG. 4c. In such an arrangement, the individual opposing pins 415 and 425 give the insole or sole preform its shape due to their position that varies across the pin matrix. Yet alternatively, the other side of the dual pin matrix may receive its shape using the foot information, while the other side may be shaped according to a predetermined shape of the footwear. This may be especially useful in manufacturing soles for shoes.

The at least essentially mirror-imaged positive and negative molds may be set and used to press the heated insole blank or preform in between. A cooling system may be integrated to the system to allow fast settling of the thermoformable material to its final shape. It should be noted that depending on the throughput time requirements, the same robot may operate multiple pressing stations and perform multiple tasks on a production line e.g. to place insole preforms on a matrix and to package pressed insoles. Specifications for the automated pressing system may be as follows. Pins may be spaced 6 mm apart, 3 mm apart, 1 mm apart, or 10 mm apart or more, and a size 48 (EUR) or a larger or a smaller insole may fit the pin matrix. The height of the each pin may be adjustable with 0.5 mm accuracy. Setting the matrices with robot may take no more than 10 s and fabricating the custom insole, sole or shoe may take no more than 60 s. The insole or sole preform may be heated to 90-100° C. with temperature at the press being 140-150° C., and the pressure being approximately 5 bar. The pins in the pin matrix may be arranged so that there is a different density of pins at different locations on the pin matrix. For the parts of the insole, which are rather flat (like toe region), a sparser matrix may be used, while areas that are less flat, a denser matrix may be used.

A single pin matrix may be used to give shape to the heated preform with the help of gravitation and vacuum based manufacturing systems. To increase manufacturing speed, a two-sided press may be used. In a two-sided press, a compressible material slab on one or both sides of the insole or sole to be manufactured may be used. The material for such slab need to be suitably selected concerning the required throughput. When using a dual pin matrix system with two opposing pin matrices, the pin matrices may be identical with the same number and position of pins, e.g. to ensure more cost effective manufacturing of the matrices.

Cooling the formed insole or sole may be used to "fix" the heated preform to the final shape rapidly enough so that the manufacturing unit achieves the set throughput specifications. Arrangements such as blowing matrices/insole with cool air can be used, or cooling with liquid or heat conduction through the pins can be used. Other cooling systems may also be implemented to the mold if necessary.

The required forces to form the insole or sole preforms may be relatively small, for example of the order of 10 or 100 Newtons or some hundreds of Newtons for the whole matrix as the insoles are floppy when heated. The shape of the pin head may be rounded or they may have other shapes like square or hexagonal. The pin head may also be larger in diameter than the pin stem, or it may be smaller in diameter than the pin stem. In order to mitigate the effect of pins leaving dents on the insoles, a sheet/membrane of elastic material may be used in front of pin matrices (e.g. silicone based). If these kind of integrating materials are used, additional and/or alternative cooling arrangements may be needed.

Figure 5:
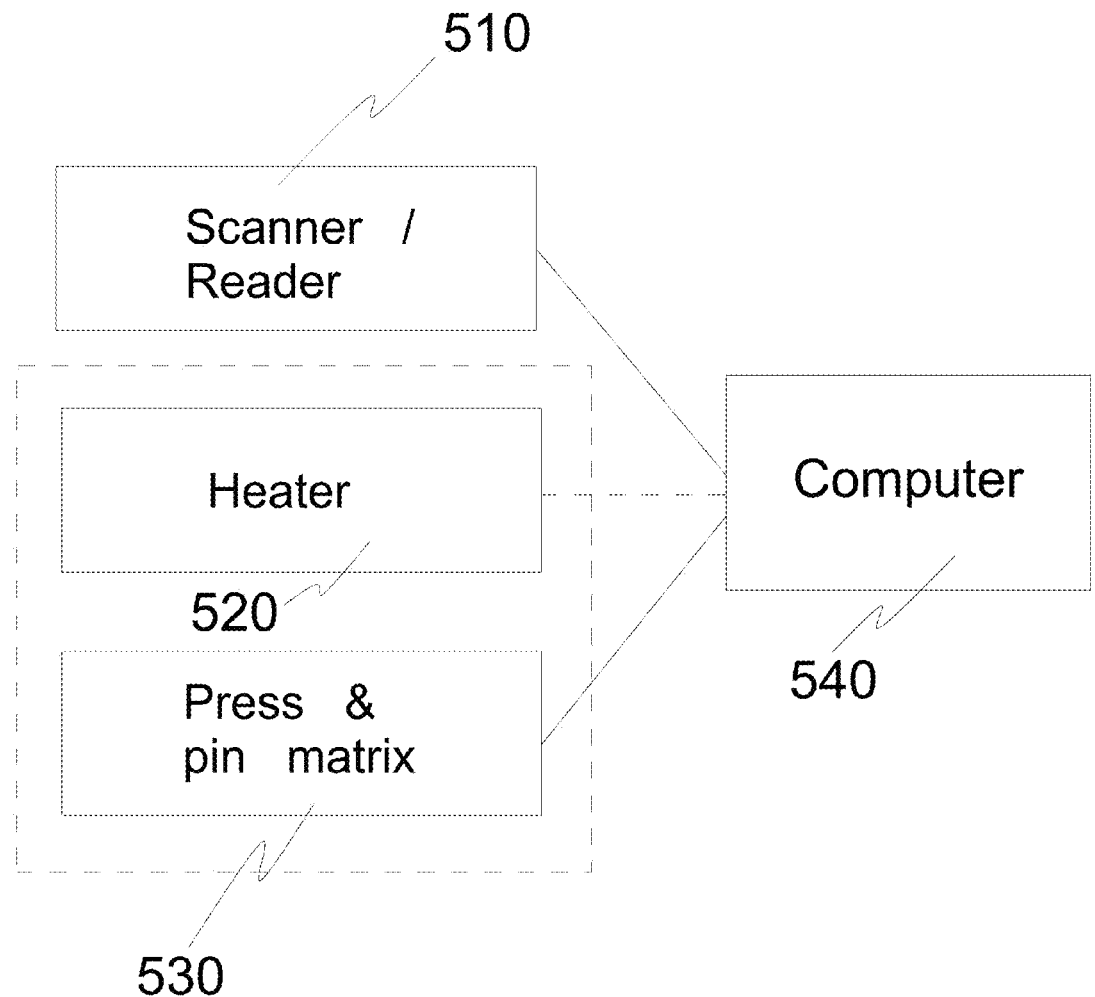
FIG. 5 shows a block diagram of an insole manufacturing system according to an embodiment of the invention.

FIG. 5 shows a block diagram of an insole manufacturing system according to an embodiment of the invention. There is a scanner or reader module 510 for determining information on the shape of the foot, as described earlier. The scanner or reader 510 may comprise computer program code (software) for implementing the scanning sequence, or the scanning sequence may be controlled externally. The scanner 510 may be connected to a computer 540 over a data connection to store information on the scanned foot shape and dimensions to a database on the computer 540. The computer may be a local computer, or it may be a remote computer in the network. There may be a user interface module (not shown) in connection with the scanner/reader and/or the computer, and the user interface module may be integrated to other foot analysis software. In addition there may be an automatic diagnostic tool that determines foot size, classifies its width (narrow, medium or wide) and pronation angle (under, neutral or over).

In the system, there may be a heating station 520 with adequate supply of warm insole or shoe sole preforms of different sizes. Heating may be done in oven-like arrangement or with infrared lamps, or with another suitable arrangement. The press and pin matrix 530 for forming the insole or sole may be in connection with the heating station or it may be separate. The press 530 may also comprise a heating unit to heat the insole preforms inside the press.

Figure 6:
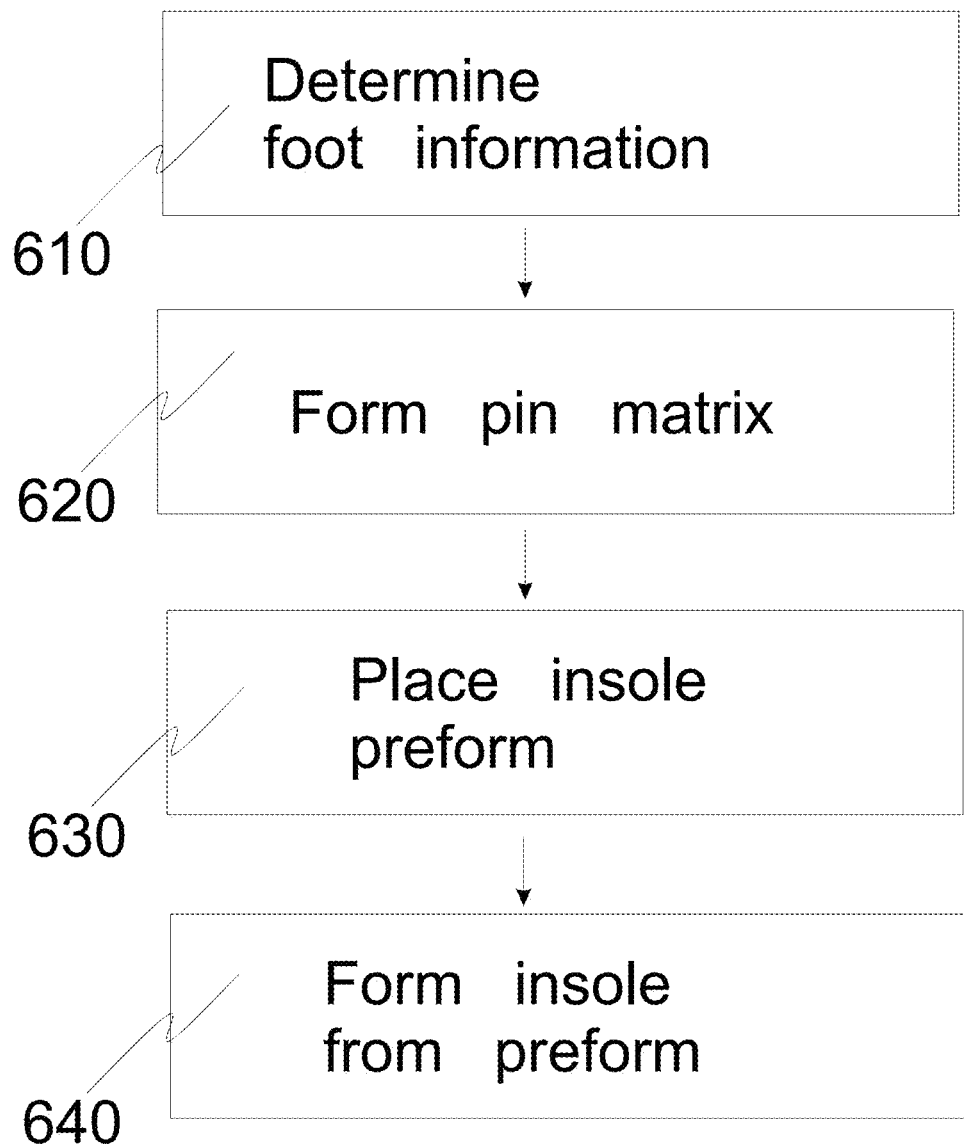
FIG. 6 shows a flow chart of the method for insole or sole manufacturing according to an embodiment of the invention.

FIG. 6 shows a flow chart of the method for insole or sole manufacturing according to an embodiment of the invention. In step 610, foot information on the shape and dimensions of a foot are determined, for example with the help of a scanner described earlier, or merely by forming this information in the memory of a computer is a scan has been performed earlier. In step 620, at least one at least partial pin matrix at least partially based on the foot information is formed, again as described earlier. Then, in step 630, an insole or sole preform is placed on the at least one at least partial pin matrix for shaping the insole preform. Finally, in step 640, the insole or sole is formed from an insole preform, being based on the foot information. Similar steps may be used for manufacturing soles for shoes or whole shoes.

Figure 7:
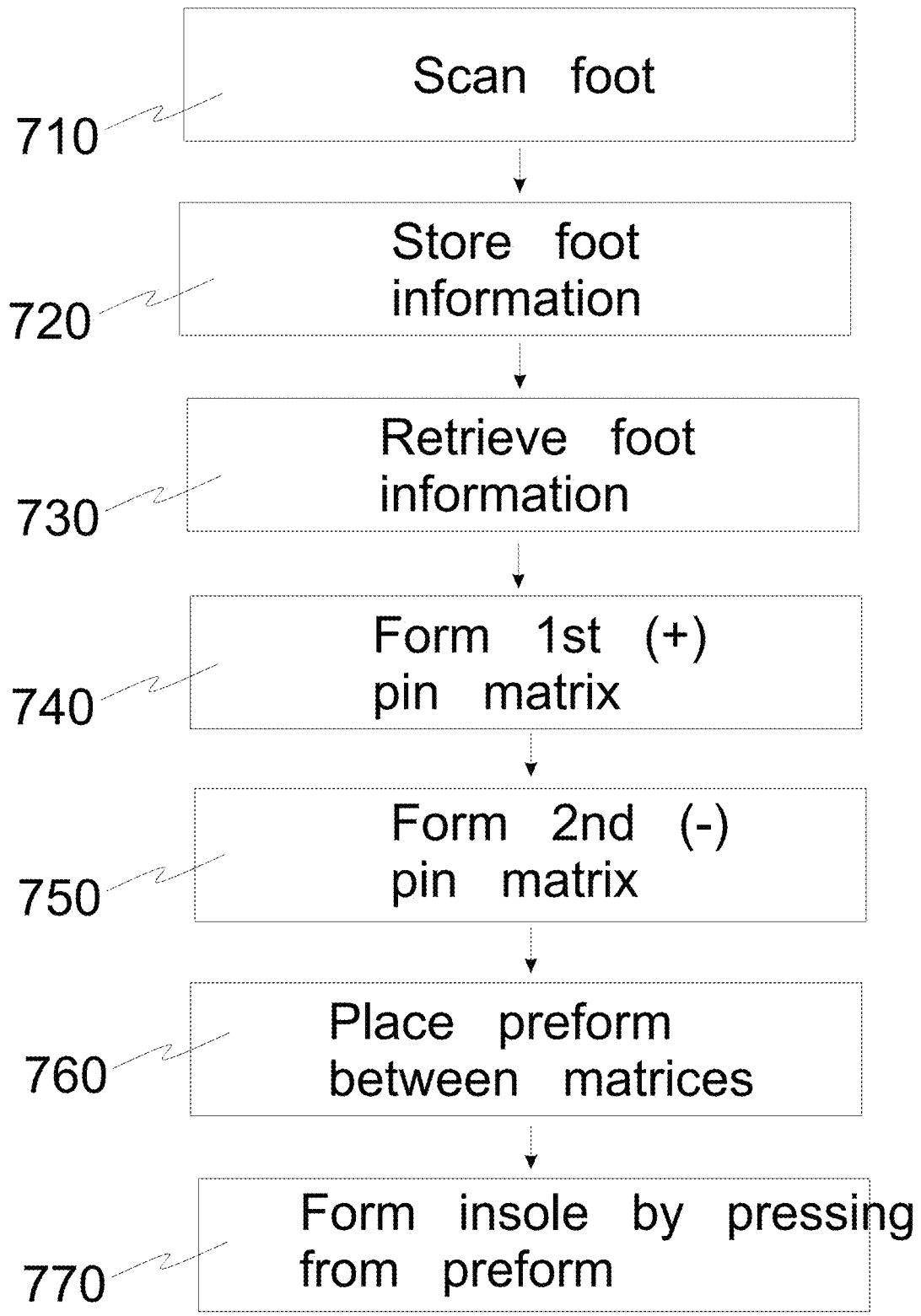
FIG. 7 shows a flow chart of the method for insole or sole manufacturing according to an embodiment of the invention.

FIG. 7 shows a flow chart of the method for insole or sole manufacturing according to an embodiment of the invention. In step 710, foot information on the shape and dimensions of a foot may be determined, for example with the help of a scanner described earlier. This information may then be stored in a memory of a computer in step 720 so that this information may be used for controlling the manufacturing of an insole. The foot information may be electronically stored at the computer in a database of foot information. In step 730, the information on the shape and dimensions of the foot may be retrieved for use in the manufacturing process. This retrieval may happen right after the forming of the information, or it may happen significantly later, e.g. at another time when a person needs a new insole. In step 740, at least one at least partial positive pin matrix at least partially based on the foot information may be formed for creating the insole. The pin matrix may be formed using a robot for example such that said robot has a roller head for rolling over the pins of the pin matrix. In step 750, at least one at least partial negative pin matrix at least partially based on the foot information is formed wherein the negative pin matrix essentially corresponds to the positive pin matrix of step 740. This may be achieved by setting the pin matrices separately, as has been explained earlier, or by setting the second pin matrix by pressing it against the first pin matrix. In step 760, an insole or sole preform may be positioned between said at least one at least partial positive pin matrix said and at least one at least partial negative pin matrix for shaping said insole or sole preform by pressing in step 770. The position of the preform may be set accurately e.g. with the help of a robot. Similar steps may be used for manufacturing soles for shoes or whole shoes.

Figure 8A:
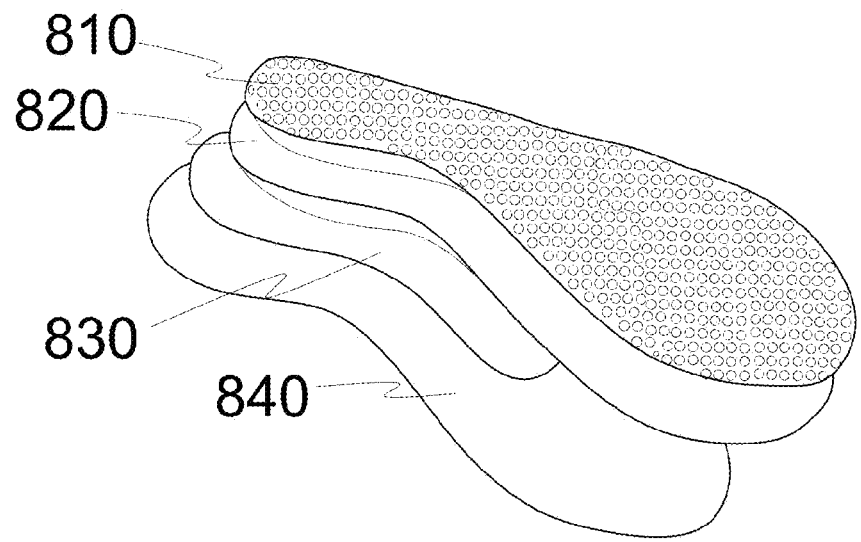
FIG. 8 shows an insole or sole manufactured according to an embodiment of the invention.
Figure 8B:
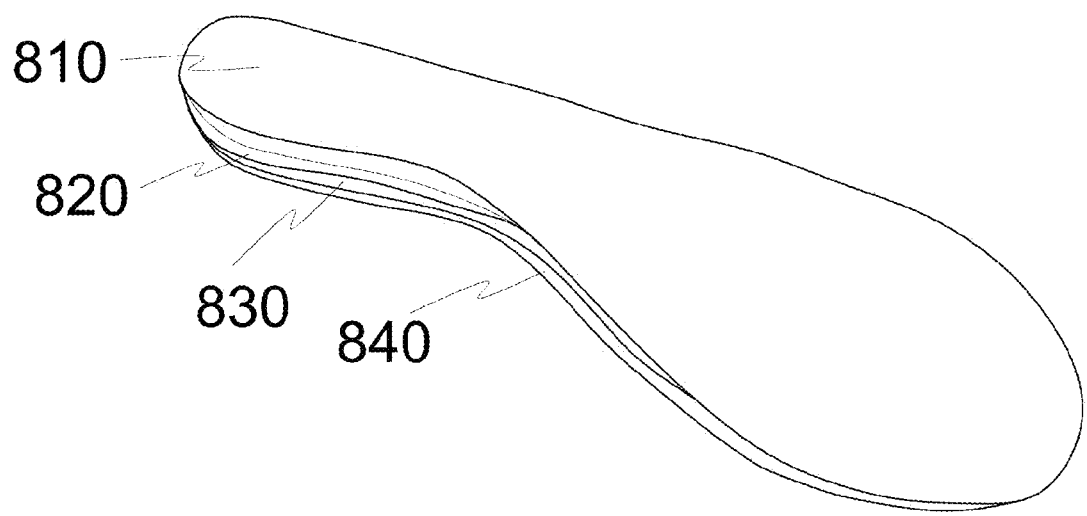

FIG. 8 shows an insole or a sole manufactured according to an embodiment of the invention. A preform (blank) insole has at least one layer, which is made of thermoplastic material and reaches out at least from under the heel to under the plantar arch of the target person's foot. Advantageously two, three or four material layers that are connected together are used in the perform insole for comfort. The upper layer 810 of the preform insole is placed against the foot and the lower layer 840 is placed against the shoe. Materials of these two layers can be selected among any common materials used in insoles. For example, the lower layer may be constructed from a known material such as Rheluflex (trademark of Rhenoflex GmbH Ltd) comprising non-woven polyester as a carrier, ionomer resin-ethylvinylacetate blend as an extruded core, and EVA-Hotmelt as an adhesive.

The middle layer 830 of the insole (in case of three layers) is made of thermoplastic. The used thermoplastic can be selected from a large group of known thermoplastics. A significant property for the thermoplastic is the temperature, so-called glass transition temperature, where the thermoplastic becomes plastic and on the other hand turns back to solid form when the temperature is decreasing after shaping the insole. The glass transition temperature is typically lower than polymer melting temperature. Therefore, one good temperature range for shaping the preform may be between the glass transition temperature and the melting temperature. A possible temperature for the thermoplastic to become plastic is preferably somewhere under 95° C. and above 45° C. Advantageously the range is from 50° C. to 85° C. The temperature can also be as high as 150° C. Suitable materials that become or are plastic within the preferred ranges are for example thermoplastic polyesters A-PET (Amorphous polyester terephthalate) and PETG (glycol-modified polyethylene terephthalate, which is a copolyester), or such with essentially similar characteristics. Also e.g. ABS (acrylonitrile butadiene styrene), PVC (polyvinyl chloride) can be used. In addition to the first middle layer 830, there may also be another middle layer 820, or even more middle layers than two.

Thickness of the thermoplastic layer may be selected so as to provide reasonable support to the client's foot when the layer is in a rigid state. The thickness may also vary throughout the layer, if e.g. more flexibility is desired under the toe area (thinner) than the plantar arch area (thicker). Other characteristic required for the thermoplastic dictates that it should be rigid under the melting temperature. When warmed, the material will become flexible and therefore a mold with uniform properties (e.g. uniform pressing force) may be used, or a mold with non-uniform properties may be used e.g. to achieve varying thickness.

With reference to an embodiment shown in FIG. 8a, the middle layer 830 made of thermoplastic can cover laterally the whole area of the insole. In alternative embodiment, the layer 830 covers laterally only a part of the insole. In that option it is necessary that the thermoplastic reaches out lengthwise at least under the heel to under the plantar arch and in lateral direction advantageously almost to the whole width of the insole. As one feasible implementation, the thermoplastic layer is designed so as to reach out from under the heel to the metatarsophalangeal joint of the foot so that transverse arch can be supported. Also, a precut pad can be placed under the transverse arch when the insole is shaped to lift the transverse arch into the optimum position. However, it is advantageous to keep some range at the edge of the insole without the hard thermoplastic in case there is need for little adjustment when the insole is placed in the shoe. Also, the toe area of the insole may remain without the hard thermoplastic to enable natural movement of the foot during walking or running. Components for manufacturing insoles as shown in FIG. 8 may also be used for manufacturing shoes or soles for shoes.

Insoles and shoes manufactured according to the invention may show a better fit to the person's foot than concurrent "custom" insoles or shoes, since the concurrent insoles or shoes aren't often fully customized to the foot, but they are selected as closest match from an existing catalog. The insole or shoe according to the invention may also be shaped to correct the possible pronation problems, as in the manual version, by scanning the foot with toes-up position. This allows the person to get a corrective insole essentially fully customized to their foot shape. The insoles or shoes may also show intentional or unintentional marks from the manufacturing method with the pin matrices.

It needs to be noticed that the techniques described earlier may be used for manufacturing shoes or soles for shoes. The foot may be scanned in a manner similar to manufacturing insoles, and the manufacturing method and apparatuses for creating shoes or soles for shoes may be essentially similar to the method and apparatuses for creating insoles.

Figure 9A:
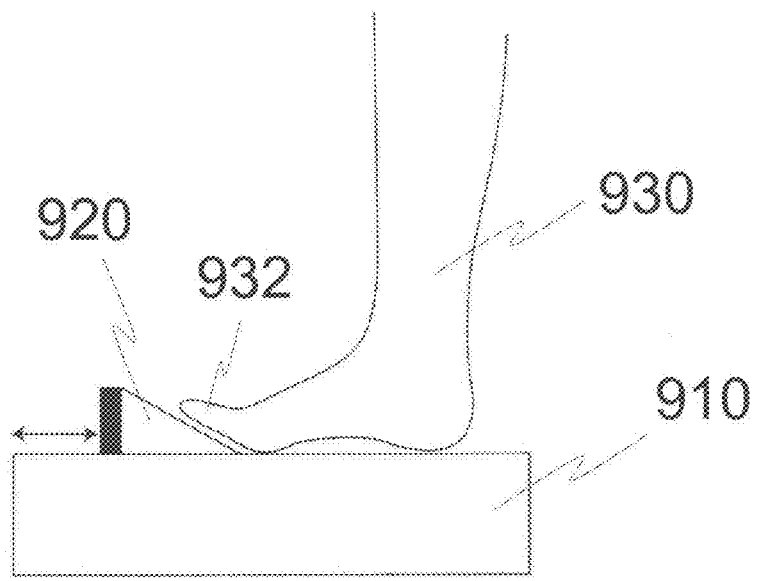
FIG. 9 shows a device and an arrangement for scanning the foot in a natural position to achieve a good support in the ready insole or sole of a shoe.
Figure 9B:
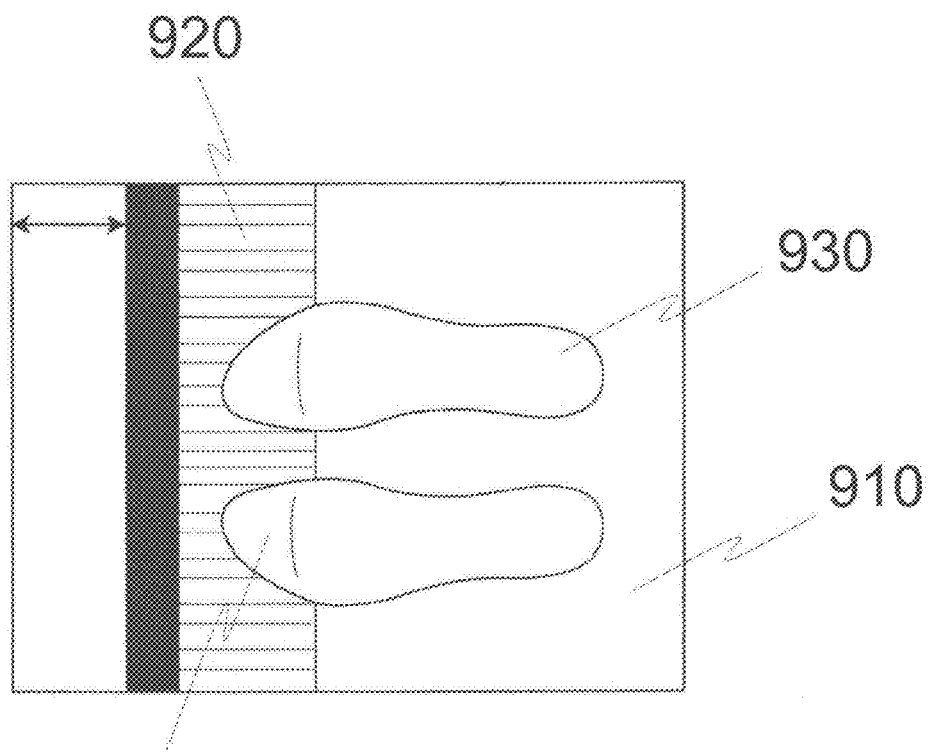

FIG. 9 shows a device and an arrangement for scanning the foot in a natural position to achieve a good support in the ready insole or footwear. The foot scanner 910 for scanning the bottom of the foot 930 may comprise a wedge 920. The wedge 920 may be movable e.g. along rails attached to the foot scanner so that it can be positioned correctly under the toes 932. Positioning the wedge 920 under the toes 932 causes the toes to tilt upwards, which in turn may cause a so-called Windlass effect. The Windlass effect may allow to use the foot's own biomechanics to guide the calcaneus (heel), medial arch and whole foot into the right position. The dorsiflexion of the first metatarsophalangeal joint (big toe) may pull the plantar aponeurosis and shorten the distance between the first metatarsal head and calcaneus. The foot's natural mechanism (Windlass effect) may therefore be used in order to scan the foot in the right position for forming the insoles or footwear.

In an embodiment according to the invention, a sole for a shoe is advantageously at least a two-piece structure including a thermoplastic layer either situated on top of the sole material or being integrated, for example embedded, within it. The one or more sole layers excluding the thermoplastic layer may comprise e.g. EVA (ethylvinylacetate) or other prior art materials; e.g. aforesaid EVA is even available in different hardnesses. If there is more than one layer the thermoplastic layer can be smaller in lateral direction than the whole sole. It is essential that the thermoplastic layer reaches out at least from under the heel to under the plantar arch of the foot the same way as with the insole. The thermoplastic materials can be selected the same way as with the insole. It may be advantageous to make at least the outer surface of the sole of some wear resistant and good friction characteristics-having material. Optionally, e.g. viscoelastic foam or other material, which may also be thermosensitive, can be used within the shoe, whereby the shoe internals also reshape in addition to mere insole and provide additional comfort/support. With this embodiment can be assured very comfortable personalised shoe that supports tightly the bone structure of the feet and ankle. This is very important if the person has a for example diabetes or rheumatism and the shoe shouldn't cause any friction or abnormal pressure to the foot.

The various embodiments of the invention can be implemented with the help of computer program code that resides in a memory and causes the relevant apparatuses to carry out the invention. For example, a manufacturing device and a scanning device may comprise circuitry and electronics for handling, receiving and transmitting data, computer program code in a memory, and a processor that, when running the computer program code, causes the device to carry out the features of an embodiment. Yet further, a remote computer may comprise circuitry and electronics for handling, receiving and transmitting data, computer program code in a memory, and a processor that, when running the computer program code, causes the remote computer to carry out the features of an embodiment.

It is obvious that the present invention is not limited solely to the above-presented embodiments, but it can be modified within the scope of the appended claims.

The invention claimed is:

1. An apparatus for forming a heated thermoformable insole, the apparatus comprising:
   a first pin matrix;
   a press configured to shape a heated insole preform by pressing;
   an integrated cooling system; and
   circuitry and electronics configured to receive digital foot information,
   wherein the first pin matrix is configured to give shape to the heated insole preform placed on the first pin matrix,
   each pin of said first pin matrix is adjustable to an appropriate position using the digital foot information received from a database, and
   the cooling system is configured to cool the shaped, heated insole by one of blowing the insole with cool air and cooling the insole with liquid or heat conduction through the pins of the pin matrix.

2. The apparatus according to claim 1, further comprising a second pin matrix essentially corresponding to the first pin matrix, the second pin matrix being configured to give shape to the heated insole preform, the apparatus being configured to give shape to the heated insole preform by pressing the heated insole preform between the first pin matrix and the second pin matrix.

3. The apparatus according to claim 2, further comprising one or more processors configured to receive information on a shape of a foot, the information being obtained from the already-existing insole in digital form, the one or more processors being configured to adapt at least one of the first pin matrix and the second pin matrix to give shape to the heated insole preform by moving pins of at least one of the first pin matrix and the second pin matrix according to the shape information on the shape of the foot.

4. The apparatus according to claim 3, wherein at least the first pin matrix comprises a locking mechanism to lock pins into place.

5. The apparatus according to claim 1, further comprising:
   a memory configured to store information on a shape of a foot; and
   a processor configured to adapt the first pin matrix according to the shape information on the shape of the foot in said memory.

6. The apparatus according to claim 1, further comprising a scanner configured to determine information on a shape of a foot.

7. The apparatus according to claim 1, further comprising a heating station configured to heat the insole preform.

* * * * *